United States Patent [19]

Ohtomo et al.

[11] 4,233,211

[45] Nov. 11, 1980

[54] FINELY POWDERED FIBROIN AND PROCESS FOR PRODUCING SAME

[75] Inventors: Koichiro Ohtomo, Takatsuki; Yukio Horikawa, Matsubara, both of Japan

[73] Assignees: Kanebo, Ltd., Tokyo; Kanebo Spun Silk, Ltd., Nagano, both of Japan

[21] Appl. No.: 79,863

[22] Filed: Sep. 28, 1979

[30] Foreign Application Priority Data

Nov. 13, 1978 [JP] Japan .................................. 53-139973

[51] Int. Cl.$^3$ ............................. C07G 7/00; A23J 1/10
[52] U.S. Cl. ..................................... 260/123.7; 424/69
[58] Field of Search ........................ 260/123.7; 424/69

[56] References Cited

U.S. PATENT DOCUMENTS

| | | | |
|---|---|---|---|
| 1,714,039 | 5/1929 | Muto et al. | 260/123.7 X |
| 2,145,855 | 2/1939 | Bley | 260/123.7 UX |

FOREIGN PATENT DOCUMENTS 519544  3/1940  United Kingdom .................. 260/123.7

OTHER PUBLICATIONS

Chem. Abstracts, vol. 47, 1953, 2942g-h, Nomura.
Chem. Abstracts, vol. 60, 1964, 14822g-h, Akyu et al.

*Primary Examiner*—Howard E. Schain
*Attorney, Agent, or Firm*—Blanchard, Flynn, Thiel, Boutell & Tanis

[57] ABSTRACT

Finely powdered high-purity fibroin and a process for producing the same are disclosed. The fibroin is a fine powder of fibroin in nonfibrous and particulate form which has an average molecular weight of not less than 50,000, particle diameters of from 1 to 100$\mu$, and a bulk density of from 0.1 to 0.7 g/cm$^3$ as measured in the dry state and which contains at least 50% by weight of hot-water-insoluble fibroin having the $\beta$-configuration. The process comprises dissolving a degummed silk material in an aqueous salt solution containing from 5 to 80% by weight of an alkali metal salt or alkaline earth metal salt; dialyzing the resulting aqueous fibroin solution; adding from 1 to 150 parts by weight of an alcohol to 100 parts by weight of the dialyzed aqueous fibroin solution having a fibroin concentration of from 3 to 20% by weight to form a gel of fibroin; dehydrating and drying the gel so formed; and then pulverizing the resulting powder. The fine powder of fibroin thus obtained is useful as an additive for cosmetic and pharmaceutical preparations.

12 Claims, No Drawings

FINELY POWDERED FIBROIN AND PROCESS FOR PRODUCING SAME

BACKGROUND OF THE INVENTION

This invention relates to finely powdered high-purity fibroin and a process for producing the same.

Powdered silk fibroin is considered to be useful as an additive for cosmetic and pharmaceutical preparations, because of its moderate moisture absorption and retention properties and its high affinity for the human skin. Currently available silk fibroin powders are generally produced by finely dividing silk thread with pulverizer. Such a silk fibroin powder consists of filamentous fibers cut in very short lengths rather than nearly globular particles and, when used as an additive for cosmetic and pharmaceutical preparations, gives rise to various difficulties. For example, in mixing the powder with other ingredients in globular form, it is so liable to aggregation that a homogeneous final product is hardly obtained. Even if such a product is obtained, it shows poor slip properties upon application to the human skin and may occasionally produce round agglomerates of silk fibroin. Thus, it can be said that these difficulties prevent us from making good use of the excellent properties of silk fibroin.

With this background, the present inventors have made repeated studies on the production of a homogeneous fine powder of fibroin in globular particulate form rather than in fibrous form. In this field of art, for example, a process for producing silk fibroin suitable for use in chromatography is disclosed in Japanese Patent Publication No. 1941/'64. This process comprises dissolving silk fibroin in a cuprammonium solution or a solution of a copper complex (for example, a cupriethylenediamine solution), neutralizing the resulting solution with an acid, and adding an alcohol to the neutralized solution to form a white precipitate of silk fibroin. As a result of confirmatory tests made by the present inventors, it has been found that this process requires a very large amount of alcohol and, moreover, the resulting precipitate is too sticky to be separated by filtration. Another process for producing a powder of silk fibroin is disclosed in Japanese Patent Publication No. 4947/'51. This process comprises dissolving degummed silk fiber in a concentrated aqueous solution of a neutral salt such as calcium nitrate, dialyzing the resulting solution, and spray-drying the colloidal solution so formed. However, the powder of silk fibroin thus obtained is abnormally hydrophilic and, therefore, unsuitable for use as an additive for cosmetic preparations.

In order to overcome the above-described difficulties, the present inventors have made great efforts to produce an improved fine powder of fibroin in nonfibrous and particulate form, and have thereby completed this invention.

BRIEF SUMMARY OF THE INVENTION

It is an object of this invention to provide a fine powder of fibroin in nonfibrous and particulate form. Another object of this invention is to provide a process for producing a fine powder of fibroin in nonfibrous and particulate form which permits its industrial production with great ease and at low cost.

In accordance with one aspect of this invention, there is provided a fine powder of regenerated fibroin in nonfibrous and particulate form which has an average molecular weight of not less than 50,000, particulate diameters of from 1 to 100$\mu$, and a bulk density of from 0.1 to 0.7 g/cm$^3$ as measured in the dry state and which contains at least 50% by weight of hot-water-insoluble fibroin having the $\beta$-configuration.

In accordance with another aspect of this invention, there is provided a process for producing such a fine powder of regenerated fibroin which comprises the steps of dissolving a degummed silk material in an aqueous salt solution containing from 5 to 80% by weight of an alkali metal salt or alkaline earth metal salt; dialyzing the resulting aqueous fibroin solution; adding from 1 to 150 parts by weight of an alcohol to 100 parts by weight of the dialyzed aqueous fibroin solution having a fibroin concentration of from 3 to 20% by weight to form a gel of fibroin; dehydrating and drying the gel so formed; and then pulverizing the resulting powder.

DETAILED DESCRIPTION OF THE PREFERRED EMBODIMENTS

The silk material which is used in the process of this invention can be cocoons, raw silk, waste cocoons, raw silk waste, bisu (unreelable cocoons), silk fabric waste, bourette, and the like. Prior to use, the silk material is degummed or freed from sericin by any conventional procedure. For example, it is washed in warm water containing a surface-active agent or any enzyme according to the need, and then dried.

Using a suitable apparatus such as kneader, the degummed silk material is dissolved in a solvent preheated to a temperature of from 60° to 95° C. and preferably from 70° to 85° C. The solvent is composed of an aqueous salt solution containing from 5 to 80% by weight of an alkali metal salt or alkaine earth metal salt, and used in an amount of from 2 to 50 parts by weight and preferably from 3 to 30 parts by weight per part by weight of the degummed silk material. The alkali metal salts and alkaline earth metal salts which can be used in the process of this invention include LiCl, LiBr, NaI, LiNO$_3$, MgCl$_2$, MgBr$_2$, Mg(NO$_3$)$_2$, ZnCl$_2$, Zn(NO$_3$)$_2$, and the like. However, CaCl$_2$ and Ca(NO$_3$)$_2$ are preferred because they permit the solubility and molecular weight of fibroin to be kept as high as possible. In the aforesaid aqueous salt solution, the concentration of the metal salt is generally from 5 to 80% by weight, preferably from 20 to 70% by weight, and most preferably from 40 to 60% by weight. If the concentration of the metal salt is less than 5% by weight, the rate of dissolution is low, while if it is greater than 80% by weight, the resulting fine powder of fibroin shows a reduction in molecular weight. It is preferable to add an alcohol to the aqueous salt solution for the purpose of further improving its dissolving powder. This alcohol may be added either before or during the dissolution of the degummed silk material, and the amount of alcohol added is generally from 20 to 60% by weight and preferably from 25 to 50% by weight.

From the resulting aqueous fibroin solution, the salt contained therein is almost completely removed by means of a dialyzer using semipermeable membranes or hollow fibers, typically made of cellophane. In order that a gel of fibroin may be formed stably and rapidly, there must be a proper correlation between the volume of the solution to be dialyzed and the surface area of the dialysis membrane. More specifically, desalting should be carried out by the use of a multilayer membrane structure or bundled hollow-fiber structure satisfying the condition expressed by $$\frac{\text{Membrane Surface Area (cm}^2\text{)}}{\text{Priming Volume (cm}^3\text{)}} \geq 10$$

where the priming volume means the internal volume within the tubing or between the layers. If the value of the above-defined ratio is less than 10, the removal of the salt through the membrane is not effected rapidly and, moreover, not a stable gel of fibroin but only a sticky precipitate is formed in the succeeding gelation step. In order to carry out the process of this invention smoothly and economically, the above-defined ratio should preferably have a value of not less than 30 and most preferably a value of not less than 50. In the case of a multilayer membrane structure, for example, it is necessary to keep the spacing between layers at 2 mm or less for the purpose of satisfying the aforesaid condition. In the case of a bundled hollow-fiber structure which is more suited to the satisfaction of the aforesaid condition, it is necessary to use hollow fibers having a diameter of 4 mm or less.

In the process of this invention, the dialyzed aqueous fibroin solution has a very low residual salt concentration of from 0.003 to 0.06% by weight, so that an extremely high purity of fibroin can be achieved.

Then, the dialyzed aqueous fibroin solution is transferred to the gelation step. First of all, the aqueous fibroin solution is adjusted to a fibroin concentration of from 3 to 20% by weight, preferably from 4 to 15% by weight, and most preferably from 5 to 10% by weight. If the fibroin concentration is less than 3% by weight, a homogeneous mass of gel is not formed and, upon addition of a large amount of alcohol, only a sticky precipitate is formed. On the other hand, if it is greater than 20% by weight, a stable mass of gel is formed but its dehydration becomes very difficult. Subsequently, the gelation step is carried out. In accordance with this invention, a homogeneous mass of gel can be formed by the addition of an alcohol to the aqueous fibroin solution having an appropriate fibroin concentration within the above-defined range. The amount of alcohol added should generally be from 1 to 150% by weight, preferably from 5 to 80% by weight, and most preferably from 10 to 60% by weight based on the weight of the aqueous fibroin solution. If the amount of alcohol added is less than 1% by weight, no gel is formed and, even if it is formed, a very long time is required. On the other hand, if it is greater than 150% by weight, a sticky precipitate rather than a stable mass of gel is formed and its dehydration becomes very difficult. There is a correlation between the amount of alcohol added and the fibroin concentration of the aqueous fibroin solution. More specifically, the product of the fibroin concentration (% by weight) and the amount of alcohol added (% by weight) should generally have a value of from 10 to 1,000 and preferably from 15 to 500. The alcohol may be added to the aqueous fibroin solution, and vice versa. In either case, a homogeneous and stable mass of gel is usually formed in an instant or within several hours.

The alcohols which can be used in the process of this invention include monohydric aliphatic alcohols such as methyl alcohol, ethyl alcohol, propyl alcohol, isopropyl alcohol, butyl alcohol, pentyl alcohol, octyl alcohol, etc.; dihydric aliphatic alcohols such as ethylene glycol, diethylene glycol, triethylene glycol, etc.; and trihydric alcohols such as glycerol. However, methyl alcohol, ethyl alcohol, and isopropyl alcohol are preferred because they permit a stable mass of gel to be formed easily.

The mass of gel so formed is subjected to the dehydration step. This step is preferably carried out by the use of a centrifuge, and the stable mass of gel formed in accordance with this invention is generally dehydrated to a water content of the order of from 100 to 500% by weight based on the weight of the solid contained therein. During the dehydration step carried out by centrifugation, the mass of gel is broken to fragments of small sizes which can then be easily dried to the absolute dry state. This drying step is carried out at a temperature of from 60° to 120° C. under normal or reduced pressure.

The powder of fibroin thus obtained is subsequently pulverized by the use of a pulverizer such as pin mill or jet mill. The practice diameters should be adjusted to a range of from 1 to 100$\mu$, preferably from 4 to 80$\mu$, and most preferably from 5 to 30$\mu$. If the particle diameters are less than 1$\mu$, the resulting fine powder shows poor dispersibility and compatibility when used as an additive for cosmetic preparations, while if they are greater than 100$\mu$, the resulting fine powder has low affinity for the skin and poor slip properties on the skin. Since the present process for producing a fine powder of fibroin involves gelation followed by dehydration and drying, the resulting fibroin particles are considered to have very minute pores to which their good moisture absorption and retention properties are attributable. However, this may lead to the disadvantage that the fine powder of fibroin becomes excessively swollen in certain applications. If is desirable, therefore, to subject the resulting fine powder of fibroin to a wet heat treatment comprising exposure to saturated steam at a temperature of 50° C. or above and preferably from 80° to 120° C. This treatment may be applied either to the powder ensuing from the dehydration and drying step or to the fine powder ensuing from the pulverization step. As a result, the resulting fine powder of fibroin is increased in the degree of crystallinity and the content of hot-water-insoluble fibroin.

The fine powder of fibroin produced in accordance with this invention has a degree of crystallinity of not less than 20%, preferably not less than 30%, and most preferably not less than 40%. The degree of crystallinity was determined in the following manner: An aqueous fibroin solution containing 5% by weight of a fibroin produced in accordance with this invention was poured on a Teflon plate and then dried at a temperature of 50° C. to form a fibroin film having a thickness of about 60$\mu$. This fibroin film was regarded as amorphous (0%) while raw silk is completely crystalline (100%). The degree of crystallinity was expressed as a relative value on the scale defined between these standard points.

The fine powder of fibroin produced in accordance with this invention has a bulk density of from 0.1 to 0.7 g/cm$^3$ and preferably from 0.2 to 0.6 g/cm$^3$ as measured in the dry state. If the bulk density is less than 0.1 g/cm$^3$, the fine powder of fibroin has poor compatibility and dispersibility and, when used as an additive for cosmetic preparations, may produce a phase separation. If it is greater than 0.7 g/cm$^3$, the fine powder of fibroin is decreased in moisture absorption and retention properties. The bulk density was measured in the most closely packed state by means of a commercially available powder tester (manufactured and sold by Hosokawa Tekkosho, Ltd.).

The fine powder of fibroin produced in accordance with this invention contains at least 50% by weight, preferably at least 70% by weight, and most preferably at least 90% by weight of hot-water-insoluble fibroin having the β-configuration. If the content of hot-water-insoluble fibroin is less than 50% by weight, the fine powder is extremely hydrophilic and liable to deterioration. Moreover, when used as a base material for cosmetic preparations, it shows a high degree of stickiness and gives a disagreeable feeling to the skin. The content of hot-water-insoluble fibroin (or rate of β-configuration) was determined in the following manner: Ten g (absolute dry weight) of a fine powder of fibroin to be tested was boiled in 1 l of hot water at a temperature of 100° C. for a period of 15 minutes, and the undissolved fraction of fibroin was absolutely dried and weighed. Then, the content of hot-water-insoluble fibroin was calculated from the equation:

Content of Hot-water-insoluble Fibroin
= $W/10 \times 100$ (% by weight)

where W stands for the absolute dry weight (in g) of the undissolved fraction of fibroin.

The fine powder of fibroin produced in accordance with this invention has a high purity as well as good moisture absorption and retention properties. Accordingly, it is very useful as an additive for cosmetic and pharmaceutical preparations. It is also suitable for use as an adsorbent in pharmaceutical and hygienic applications, because the fibroin particles contained therein have very minute pores owing to the special manner of production.

The present invention is further illustrated by the following examples.

EXAMPLE 1

In this example, raw silk waste was used as the starting material for the production of fine powders of fibroin. Three kg of raw silk waste was immersed in 100 l of water containing 0.3% by weight of marseille soap, stirred at 80° C. for 1 hour, treated with a sericinolytic enzyme to remove the sericin almost completely, washed with water, and then dried.

By stirring in a kneader, 1-kg portions of raw silk waste degummed as above were dissolved in 10 kg each of aqueous calcium chloride solutions having the respective calcium chloride concentrations indicated in Table 1. As can be seen from the data of this table, the process of this invention allowed the raw silk waste to be dissolved easily. However, when the calcium chloride concentration was less than 5% by weight as in Control Runs 1-(1) and 1-(2), it was hardly dissolved even after a long period of time (24 hours or more).

The resulting aqueous fibroin solutions were then desalted by passing each of them through a dialyzer of the hollow-fiber type at a rate of 1 l/hr. This dialyzer was composed of 2,000 hollow fibers of regenerated cellulose having an internal diameter of 200μ, a membrane thickness of 20μ, and a length of 500 mm, both ends of these hollow fibers being bundled and sealed without blocking up their hollow bores. In this case, the ratio of membrane surface area ($cm^2$) to priming volume ($cm^3$) has a value of 100. After completion of the dialysis, the aqueous fibroin solutions had fibroin concentrations of 5.3–6.7% by weight and residual calcium chloride concentrations of 0.007–0.033% by weight.

The molecular weight of the fibroin contained in each of the dialyzed aqueous fibroin solutions was measured by gel permeation chromatography. When the calcium chloride concentration was greater than 80% by weight as in Control Run 1-(15), the molecular weight was reduced to the order of 40,000. In the aqueous fibroin solutions prepared in accordance with this invention, however, the fibroin contained therein had a molecular weight of not less than 50,000 and showed no appreciable degree of hydrolysis.

TABLE 1

|  |  | Calcium Chloride Concentration* (wt. %) | Amount of Ethyl Alcohol Added** (wt. %) | Temperature (°C.) | Time (hr) | Solubility*** | Molecular Weight ($\times 10^4$) |
|---|---|---|---|---|---|---|---|
| 1-(1) | Control Run | 3 | 0 | 95 | 24 | X | — |
| 1-(2) | " | 3 | 30 | 85 | 24 | X | — |
| 1-(3) | Test Run | 5 | 30 | 85 | 5 | Δ | 8 |
| 1-(4) | " | 10 | 30 | 80 | 5 | Δ | 9 |
| 1-(5) | " | 30 | 30 | 80 | 2 | O | 9 |
| 1-(6) | " | 40 | 0 | 95 | 2 | O | 7.5 |
| 1-(7) | " | 40 | 30 | 80 | 2 | ◎ | 9.5 |
| 1-(8) | " | 50 | 0 | 95 | 1 | O | 8 |
| 1-(9) | " | 50 | 30 | 80 | 1 | ◎ | 10 |
| 1-(10) | " | 50 | 50 | 95 | 1 | ◎ | 10 |
| 1-(11) | " | 60 | 0 | 80 | 1 | O | 8.5 |
| 1-(12) | " | 60 | 30 | 80 | 1 | ◎ | 11 |
| 1-(13) | " | 60 | 30 | 70 | 1 | ◎ | 11 |
| 1-(14) | " | 80 | 50 | 80 | 1 | ◎ | 5.5 |
| 1-(15) | Control Run | 90 | 60 | 80 | 1 | ◎ | 4 |

*Expressed as percentages based on the weight of the aqueous calcium chloride solution, exclusive of ethyl alcohol.
**Expressed as percentages based on the weight of the aqueous calcium chloride solution.
***Rated as insoluble (X), sparingly soluble (Δ), soluble (O), or very soluble (◎).

EXAMPLE 2

The procedure of Test Run 1-(12) in Example 1 was repeated except that the calcium chloride was replaced by calcium nitrate. After dialysis, the resulting aqueous fibroin solution had a fibroin concentration of 6.2% by weight and a residual calcium nitrate concentration of 0.015% by weight. This aqueous fibroin solution was either concentrated or diluted with water to prepare a series of aqueous fibroin solutions having the respective fibroin concentrations indicated in Table 2.

An alcohol was added to each of the above aqueous fibroin solutions and the form of the resulting gel was observed. When the fibroin concentration was less than 3% by weight as in Control Runs 2-(1) and 2-(2) or when the amount of alcohol added was greater than 150% by weight of the aqueous fibroin solution as in Control Runs 2-(6), 2-(14) and 2-(18), not a homogeneous mass of gel but a white precipitate was formed. This precipitate was too sticky to be separated by conventional filtration under reduced pressure. When it was placed in a cloth bag and then centrifuged, it aggregated into a bulky and sticky mass which was very difficult of dehydration and drying. On the other hand, when the amount of alcohol added was less than 1 by weight as in Control Runs 2-(8) and 2-(15), no gelation was recognized even after the mixture was allowed to stand for a whole day and night. Furthermore, when the fibroin concentration was greater than 20% by weight as in Control Run 2-(22), the resulting mass of gel was so tough that it could hardly be dehydrated by centrifugation.

However, the process of this invention allowed a homogeneous mass of gel to be formed in an instant or within several hours after the addition of an alcohol. When dehydrated by centrifugation, the mass of gel was broken to fragments having sizes of the order of several millimeters and water contents of 110–480% by weight. Methyl alcohol, ethyl alcohol, and isopropyl alcohol made no substantial differences in the form of the resulting gel and the requirements for further treatment. The dehydrated gel was dried in a hot-air oven set at 90°–100° C. or a vacuum dryer set at 70° C. to obtain a fine granular product of fibroin suitable for direct pulverization with a jet mill. Subsequently, the granular product was subjected to a wet heat treatment comprising exposure to saturated steam at 120° C. for 20 minutes, and then pulverized with a jet mill to obtain a fine powder of fibroin consisting of nearly globular particles, 98% or more of which had diameters of 5–40$\mu$.

When measurements of the bulk density were made, all the fine powders of fibroin, except that produced in Control Run 2-(22), were found to have values within the range of 0.1–0.7 g/cm$^3$. The reason for this seems to be that the fibroin particles contained therein had minute pores owing to the special manner of production in which a powder is derived from a homogeneous mass of gel.

In all the fine powders of fibroin produced in accordance with this invention, the content of hot-water-insoluble fibroin or rate of $\beta$-configuration was found to be not less than 70% by weight and the degree of molecular orientation was found to be not greater than one-half that of natural silk.

Furthermore, measurements of the rate of moisture absorption were made. More specifically, a sample of each fine powder of fibroin was allowed to stand in an atmosphere having a temperature of 20° C. and a relative humidity of 65%, and the amount of water absorbed was measured after 2 hours. For purposes of comparison, a fine powder of fibroin produced by finely dividing silk yarn with a pulverizer had a rate of moisture absorption of 2–3% by weight as measured by the same method.

The results of these measurements are given in Table 2.

TABLE 2

| | Fibroin Concentration (wt. %) | Addition of Alcohol Type* | Addition of Alcohol Amount (wt. %) | Gelation Time (min.) | Form of Gel | Dehydration by Centrifugation Water Content** (wt. %) | Dehydration by Centrifugation Degree of Dehydration*** (wt. %) | Bulk Density (g/cm³) | Rate of Moisture Absorption (wt. %) | Content of Hot-Water-insoluble Fibroin (%) | Degree of Crystallinity (%) |
|---|---|---|---|---|---|---|---|---|---|---|---|
| 2-(1) Control Run | 2 | E | 10 | — | Precipitate | — | — | — | — | 2 | 0 |
| 2-(2) " | 2 | E | 50 | — | " | — | — | — | — | 7 | 0 |
| 2-(3) Test Run | 3 | E | 10 | 180 | Soft mass | 480 | 87 | 0.59 | 4.2 | 76 | 43 |
| 2-(4) " | 5 | E | 10 | 180 | " | 450 | 79 | 0.44 | 5.5 | 79 | 46 |
| 2-(5) " | 5 | E | 50 | 5 | " | 320 | 96 | 0.27 | 6.1 | 98 | 68 |
| 2-(6) Control Run | 5 | E | 180 | — | Precipitate | — | — | — | — | 10 | 1 |
| 2-(7) Test Run | 5 | M | 20 | 20 | Soft mass | 400 | 83 | 0.41 | 5.7 | 93 | 62 |
| 2-(8) Control Run | 10 | E | 0.5 | 1,440 | No gelation | — | — | — | — | — | — |
| 2-(9) Test Run | 10 | E | 2 | 300 | Somewhat hard mass | 410 | 55 | 0.54 | 4.5 | 74 | 43 |
| 2-(10) " | 10 | E | 10 | 180 | " | 270 | 73 | 0.39 | 5.3 | 88 | 48 |
| 2-(11) " | 10 | E | 20 | 20 | " | 150 | 86 | 0.44 | 5.1 | 90 | 60 |
| 2-(12) " | 10 | E | 50 | 5 | " | 110 | 92 | 0.21 | 6.2 | 98 | 65 |
| 2-(13) " | 10 | E | 150 | 1 | Soft mass | 180 | 92 | 0.50 | 4.8 | 83 | 42 |
| 2-(14) Control Run | 10 | E | 200 | — | Precipitate | — | — | — | — | 17 | 3 |
| 2-(15) " | 10 | M | 0.3 | — | No gelation | — | — | — | — | — | — |
| 2-(16) Test Run | 10 | M | 20 | 20 | Somewhat hard mass | 200 | 82 | 0.45 | 5.2 | 85 | 48 |
| 2-(17) " | 10 | P | 20 | 20 | " | 210 | 81 | 0.45 | 5.1 | 77 | 43 |
| 2-(18) Control Run | 10 | P | 200 | — | Precipitate | — | — | — | — | 30 | 7 |
| 2-(19) Test Run | 15 | E | 20 | 15 | Somewhat hard mass | 200 | 71 | 0.41 | 5.0 | 81 | 48 |
| 2-(20) " | 15 | M | 20 | 15 | " | 190 | 73 | 0.42 | 5.0 | 81 | 46 |
| 2-(21) " | 20 | E | 20 | 15 | " | 260 | 48 | 0.62 | 3.7 | 70 | 41 |
| 2-(22) Control Run | 25 | E | 20 | 15 | Hard mass | — | — | 0.76 | 2.9 | 38 | 12 |

*E stands for ethyl alcohol, M for methyl alcohol, and P for isopropyl alcohol.
**Defined as the solvent content of the gel.
***Defined as (the amount of solvent removed by centrifugation)/(the amount of solvent used during gelation) × 100.

EXAMPLE 3

One kg of spun silk waste (bourette) was immersed in 30 l of water containing 0.5% by weight of marseilles soap, stirred at 100° C. for 1 hour to remove the sericin and oily matter almost completely, washed thoroughly with water, and then dried at 70° C. In a kneader having a capacity of 50 l, a solution of 7.5 kg of calcium chloride in 5 kg of water and 4 kg of ethyl alcohol was prepared, and 3 kg of bourette degummed as above was dissolved therein by stirring at 80° C. for 1 hour. After completion of the dissolution, 9 kg of water preheated to 80° C. was added. The resulting fibroin solution was filtered to remove any insoluble foreign matter such as chrysalis refuse, and then desalted by passing it through the same dialyzer of the hollow-fiber type as used in Example 1. The aqueous fibroin solution thus obtained had a fibroin concentration of 6.2% by weight and a residual calcium chloride concentration of 0.021% by weight.

When 10 kg of ethyl alcohol was added, with stirring, to 40 kg of an aqueous fibroin solution prepared as above and the resulting mixture was allowed to stand, a homogeneous mass of gel was formed in 20 minutes. This mass of gel was placed in a bag made of polyester fabric and then centrifuged to obtain fragments of gel having water contents of 250–350% by weight. After the dehydrated gel was dried in a vacuum dryer set at 80° C., a part of the resulting granular product was directly pulverized with a jet mill and the rest was subjected to a wet heat treatment comprising exposure to saturated steam at 100° C. for 10 minutes and then pulverized with a jet mill. Thus, a variety of fine powders of fibroin having the respective particle diameter ranges indicated in Table 3 were obtained.

Using a mixer, each of the above fine powders of fibroin was blended with an equal weight of a commercially available fine powder of talc, and the compatibility and dispersibility of the resulting blend were examined under the microscope. It was found that its dispersibility became poor when the diameters of fibroin particles were excessively large or small. Especially when the fine powder of fibroin had particle diameters of less than 1μ as in Control Run 3-(1) or when it had particle diameters of greater than 100μ as in Control Runs 3-(12) and 3-(13), the fibroin and the talc tended to aggregate separately in the form of spots. When the diameters of fibroin particles were within the range of 1–100μ and particularly 4–80μ as taught by this invention, the fibroin and the talc showed very good compatibility and dispersibility. In addition, a sample of each fine powder of fibroin was placed on a hand and rubbed with fingers. As a result, the fine powders of fibroin produced in accordance with this invention spread uniformly over the skin without any appreciable degree of agglomeration and showed good slip properties. Especially the fine powders of fibroin subjected to a wet heat treatment were superior in slip and non-agglomeration properties to those subjected to no wet heat treatment. This is presumed to be due to the enhancement of crystallinity of fibroin caused by the wet heat treatment. In fact, when the fine powders of fibroin produced in Test Runs 3-(4) and 3-(5) were examined by X-ray diffraction analysis, the degree of crystallinity was 28% in the fine powder of fibroin subjected to no wet heat treatment and 45% in that subjected to a wet heat treatment. Moreover, the content of hot-water-insoluble fibroin or rate of β-configuration was 52% by weight in the fine powder of fibroin subjected to no wet heat treatment and 98% by weight in that subjected to a wet heat treatment. However, the fine powder of fibroin produced in Control Run 3-(1), which had particle diameters of less than 1μ, formed round agglomerates when placed on the skin and rubbed with fingers. On the other hand, the fine powders of fibroin produced in Control Runs 3-(12) and 3-(13), which had particle diameters of greater than 100μ, felt rough and showed very poor slip properties.

TABLE 3

| | | Particle Range Diameter (μ) | Wet Heat Treatment at 110° C. for 10 min. | Bulk Density (g/cm$^3$) | Dispersibility with Talc* | Slip on the Skin* |
|---|---|---|---|---|---|---|
| 3-(1) | Control Run | <1 | Done | 0.16 | X | X (Agglomeration) |
| 3-(2) | Test Run | 1–10 | " | 0.22 | Δ | Δ |
| 3-(3) | " | 4–25 | " | 0.29 | O | ◎ |
| 3-(4) | " | 5–30 | " | 0.44 | ◎ | ◎ |
| 3-(5) | " | 5–30 | Not done | 0.37 | ◎ | ◎ |
| 3-(6) | " | 10–50 | Done | 0.51 | ◎ | ◎ |
| 3-(7) | " | 10–50 | Not done | 0.48 | O | O |
| 3-(8) | " | 25–80 | Done | 0.55 | ◎ | O |
| 3-(9) | " | 5–100 | " | 0.53 | O | Δ |
| 3-(10) | " | 5–100 | Not done | 0.50 | Δ | Δ |
| 3-(11) | " | 50–100 | Done | 0.64 | Δ | Δ |
| 3-(12) | Control Run | 70–150 | " | 0.78 | X | X |
| 3-(13) | " | >100 | " | 0.83 | X | X |

*Rated as very good (◎), good (O), inadequate (Δ), or poor (X).

What is claimed is:

1. A fine powder of regenerated fibroin in nonfibrous and particulate form which has an average molecular weight of not less than 50,000, a degree of molecular orientation equal to not greater than one-half that of natural silk thread, particle diameters of from 1 to 100μ, and a bulk density of from 0.1 to 0.7 g/cm$^3$ as measured in the dry state and which contains at least 50% by weight of hot-water-insoluble fibroin having the β-configuration.

2. A fine powder of regenerated fibroin as claimed in claim 1 which has a degree of crystallinity of not less than 20%.

3. A fine powder of regenerated fibroin as claimed in claim 1 which has a degree of crystallinity of not less than 40%.

4. A fine powder of regenerated fibroin as claimed in claim 1 which has an average molecular weight of not less than 80,000.

5. A fine powder of regenerated fibroin as claimed in claim 1 which has a bulk density of from 0.2 to 0.6 g/cm$^3$.

6. A fine powder of regenerated fibroin as claimed in claim 1 which contains at least 90% by weight of hot-water-insoluble fibroin having the β-configuration.

7. A process for producing a fine powder of regenerated fibroin in nonfibrous and particulate form which has an average molecular weight of not less than 50,000, a degree of molecular orientation equal to not greater than one-half that of natural silk thread, particle diameters of from 1 to 100μ, and a bulk density of from 0.1 to 0.7 g/cm$^3$ as measured in the dry state and which contains at least 50% by weight of hot-water-insoluble fibroin having the β-configuration, the process comprising the steps of dissolving a degummed silk material in an aqueous salt solution containing from 5 to 80% by weight of an alkali metal salt or alkaline earth metal salt; dialyzing the resulting aqueous fibroin solution; adding from 1 to 150 parts by weight of an alcohol to 100 parts by weight of the dialyzed aqueous fibroin solution having a fibroin concentration of from 3 to 20% by weight to form a gel of fibroin; dehydrating and drying the gel so formed; and pulverizing the resulting powder.

8. A process as claimed in claim 7 wherein the alkaline earth metal salt is calcium nitrate or calcium chloride.

9. A process as claimed in claim 7 wherein the alcohol is methyl alcohol, ethyl alcohol, or isopropyl alcohol.

10. A process as claimed in claim 7 wherein the gel of fibroin is dehydrated by centrifugation and then dried under normal or reduced pressure.

11. A process as claimed in claim 7 wherein the powder resulting from the dehydration and drying step is subjected to a wet heat treatment comprising exposure to saturated steam at a temperature of 50° C. or above.

12. A process as claimed in claim 7 wherein the dialysis step is carried out by the use of a multilayer membrane structure or bundled hollow-fiber structure satisfying the condition expressed by $$\frac{\text{Membrane Surface Area (cm}^2\text{)}}{\text{Priming Volume (cm}^3\text{)}} \geq 10$$

* * * * *